US009658153B2

(12) United States Patent
Goto et al.

(10) Patent No.: US 9,658,153 B2
(45) Date of Patent: May 23, 2017

(54) FLOW CELL AND LIQUID ANALYZER

(71) Applicant: HITACHI HIGH-TECHNOLOGIES CORPORATION, Tokyo (JP)

(72) Inventors: Yusuke Goto, Tokyo (JP); Masao Kamahori, Tokyo (JP); Yu Ishige, Tokyo (JP); Hiroshi Sasaki, Tokyo (JP); Hideyuki Akiyama, Tokyo (JP); Shintaro Kubo, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 520 days.

(21) Appl. No.: 14/363,366

(22) PCT Filed: Oct. 30, 2012

(86) PCT No.: PCT/JP2012/077985
§ 371 (c)(1),
(2) Date: Jun. 6, 2014

(87) PCT Pub. No.: WO2013/084626
PCT Pub. Date: Jun. 13, 2013

(65) Prior Publication Data
US 2014/0332674 A1     Nov. 13, 2014

(30) Foreign Application Priority Data
Dec. 8, 2011   (JP) ................................ 2011-269147

(51) Int. Cl.
| | |
|---|---|
| *G01N 21/00* | (2006.01) |
| *G01N 21/31* | (2006.01) |
| *G01N 30/74* | (2006.01) |
| *G01N 21/05* | (2006.01) |
| *G01N 1/00* | (2006.01) |

(Continued)

(52) U.S. Cl.
CPC ............... *G01N 21/31* (2013.01); *G01N 1/00* (2013.01); *G01N 21/05* (2013.01); *G01N 30/74* (2013.01);
(Continued)

(58) Field of Classification Search
CPC .................. G01N 21/05; G01N 30/74; G01N 2021/0346; G01N 2030/746;
(Continued)

(56) References Cited

U.S. PATENT DOCUMENTS

| | | | |
|---|---|---|---|
| 5,184,192 A | 2/1993 | Gilby et al. | |
| 5,570,447 A | 10/1996 | Liu | |

(Continued)

FOREIGN PATENT DOCUMENTS

| | | | |
|---|---|---|---|
| JP | 2002-156326 A | 5/2002 | |
| JP | 2002-296175 A | 10/2002 | |

(Continued)

OTHER PUBLICATIONS

Kamahori et al., "High-Sensitivity Micro Ultraviolet Absorption Detector for High-Performance Liquid Chromatography", Journal of Chromatography, 1989, pp. 227-232, vol. 465.

(Continued)

*Primary Examiner* — Tri T Ton
(74) *Attorney, Agent, or Firm* — Mattingly & Malur, PC

(57) ABSTRACT

To prevent lowering of sensitivity of a flow cell based on total reflection of light at an outer face of a glass capillary at a joint part with a pipe, the flow cell includes, at joint parts with a pipe 605 to introduce solution to a glass capillary 601 and with a pipe to discharge solution from the capillary, an inorganic material layer 602 that reflects measurement light to modify the outer face of the glass capillary as well as a reinforcement layer 711 to modify the surface thereof.

13 Claims, 10 Drawing Sheets

(51) Int. Cl.
*G01N 21/3577* (2014.01)
*G01N 21/03* (2006.01)

(52) U.S. Cl.
CPC ..... *G01N 21/0303* (2013.01); *G01N 21/3577* (2013.01); *G01N 2021/0346* (2013.01); *G01N 2021/052* (2013.01)

(58) Field of Classification Search
CPC .. G01N 21/0303; G01N 21/0317; G01N 1/00; G01N 2021/052; G01N 21/31; G01N 21/3577; G02B 6/032; G02B 6/381; G02B 6/2808; Y10S 138/03
See application file for complete search history.

(56) References Cited

U.S. PATENT DOCUMENTS

| | | |
|---|---|---|
| 6,188,813 B1 | 2/2001 | Dourdeville et al. |
| 6,542,231 B1 | 4/2003 | Garrett |
| 2001/0010747 A1 | 8/2001 | Dourdeville et al. |
| 2002/0102183 A1 | 8/2002 | Uchimura |
| 2006/0139632 A1 | 6/2006 | Gerner et al. |
| 2009/0176084 A1 | 7/2009 | Yoshihara et al. |
| 2012/0267042 A1 | 10/2012 | Okafuji et al. |

FOREIGN PATENT DOCUMENTS

| | | |
|---|---|---|
| JP | 2002-536673 A | 10/2002 |
| JP | 2008-525817 A | 7/2008 |
| JP | 2009-53691 A | 3/2009 |
| WO | 2011/043361 A1 | 4/2011 |

OTHER PUBLICATIONS

Tsunoda et al., "The Possibility of Signal Enhancement in Liquid Absorption Spectrometry with a Long Capillary Cell Utilizing Successive Total Reflection at the Outer Cell Surface", Applied Spectroscopy, 1989, pp. 49-55, vol. 43.

1
FLOW CELL AND LIQUID ANALYZER

TECHNICAL FIELD

The present invention relates to flow cells for spectroscopic analysis of a sample, and particularly relates to a flow cell for spectroscopic analysis that is used for a liquid analyzer.

BACKGROUND ART

Spectroscopic analyzers to analyze a sample by spectroscopy with ultraviolet, visible or infrared light, which are included in liquid analyzers such as a liquid chromatography analyzer, are provided with a flow cell, and these analyzers perform absorption spectrometry or fluorescence analysis using this flow cell. A flow cell with a longer optical path length typically shows higher analytical sensitivity. A flow cell with a long optical path length, however, has a problem that measurement light impinges on the inner wall of the channel, and so the amount of measurement light passing through the flow cell decreases and so the sensitivity deteriorates. Especially in the case of an analyzer based on absorption spectroscopy, measurement light impinging on the inner wall of the flow cell will cause disordered light reflection/light scattering or light absorption, thus increasing noise often (Non-Patent Literature 1). That is, there is a known problem that solution changes in refractive index because of external factors such as temperature change, pressure change or composition change of the solution, which changes the ratio of such reflected light or scattered light with respect to the incident light, and such a change is detected as apparent change in absorbance, i.e., noise or drift.

In order to solve these problems, a method to totally reflect measurement light at a wall face of the channel has been proposed for improved sensitivity. This method can be roughly classified into two types of including a light reflective layer at an inner wall of the channel and including a light reflective layer at an outer wall of the channel. For the former method, a method proposed is to apply an organic material having a refractive index lower than that of water (refractive index 1.33) that is the most frequently used for spectroscopic analysis, particularly Teflon (registered trademark) AF as a fluorine polymer, to the inner wall of the channel as a light reflective layer (Patent Literature 1, Patent Literature 2). Such a structure achieves total reflection of measurement light 104 at the interface between solution 103 in the flow cell and a light reflective layer 102 disposed at a channel inner wall 101 as shown in FIG. 1. This method unfortunately fails to keep the total reflection conditions of the light if the inner wall of the channel adsorbs dirt, and so sensitivity deteriorates. Additionally, it is difficult to apply an organic material of a low refractive index that is required for total light reflection at the inner wall of the channel in a flow cell having a long optical path length so as to exert such optical characteristics, and so there is upper limit for the length of an optical path that can be increased.

For the latter method, a proposed method is to use a flow cell having a channel that is made of a glass capillary that does not absorb measurement light and dispose a light reflective layer at the outer face of the glass capillary, whereby as shown in FIG. 2, measurement light 104 propagating through solution 103 is totally reflected at the interface between the outer face of the glass capillary 201 and the light reflective layer 202. Since this is total light reflection based on a difference in refractive index between the solution and the light reflective layer via the glass capillary, and as its advantages, it is easy to lengthen the optical path, and there is no upper limit in theory for the length of the optical path that can be increased. For instance, a method proposed is to use air as the light reflective layer to realize total reflection of measurement light at the interface between the outer wall of the channel and air (Non-Patent Literature 2). FIG. 3 shows a typical structure of such a flow cell. The flow cell as a whole is configured to include the glass capillary 201, two optical fibers 302, 303, on which measurement light is incident for receiving, two pipes 304, 305 to introduce and discharge solution, and joint parts 306 and 307 having two channels to joint them. Measurement light propagates through the flow cell while being totally reflected at the interface between the outer face of the glass capillary 201 and air due to a difference in refractive index between solution and air. As another structure proposed is a flow cell including a light reflective layer provided at the surface of a glass capillary made of Teflon (registered trademark) AF (Patent Literature 3). When manufacturing these flow cells, the joint parts have to be connected without leakage of liquid, the joint parts including a channel to connect the flow cell with a glass capillary, an optical fiber and a pipe. To this end, there are known methods to apply pressure to them using mechanical components such as a ferrule and a nut to block a gap between the components and to provide a joint part made of a thermal-dissolving resin and apply heat to it, thus blocking a gap between the components with the dissolving resin for connection. As compared with the former, the latter method reduces the number of components and man-hours, and so the latter thermal welding is preferably used.

CITATION LIST

Patent Literatures

Patent Literature 1: U.S. Pat. No. 5,184,192 A
Patent Literature 2: U.S. Pat. No. 6,542,231 A
Patent Literature 3: U.S. Pat. No. 5,570,447 A

Non Patent Literatures

Non Patent Literature 1: J. Chromatogr. 465, 227 (1989)
Non Patent Literature 2: Appl. Spectrosc. 43, 49 (1989)

SUMMARY OF INVENTION

Technical Problem

The method including a light reflective layer at the outer wall of the channel has a problem at a part in the vicinity of the joint part. FIG. 4 is a cross sectional view in the vicinity of the joint part of a flow cell including a light reflective layer that is air. A joint part 306 filled with solution 103 internally includes a glass capillary 201, an optical fiber 302 and a pipe 304 therein as shown in FIG. 4. This structure, however, fails to meet the conditions for total reflection of light at a part where the outer face of the glass capillary 201 meets the joint part 306, and so the amount of measurement light 104 attenuates and the sensitivity deteriorates.

Trial to solve this problem using an organic material with a low refractive index such as Teflon (registered trademark) AF as a light reflective layer will cause the problems specific to an organic material. One of the problems relates to manufacturing. Since a thermal-dissolving resin used as a material of the joint part often has a melting point that is higher than an upper limit temperature for use of an organic material that is often used as the light reflective layer and is very close to the decomposition temperature thereof. For instance, polyether ether ketone resins as a typical example of the thermal-dissolving resin have the melting point of about 340 to 370° C., whereas Teflon (registered trademark) AF as a typical example of the organic material used for the light reflective layer has the upper limit temperature for use of 285° C. and the decomposition temperature of 360° C. Since temperatures of the components often rise above the melting point of the thermal-dissolving resin during thermal welding, a flow cell manufactured under such conditions will have the problems that the organic material will lose the function as the light reflective layer or the organic material itself disappears.

Another problem relates to long-term stability of the performance. As compared with the thermal coefficient of expansion of a glass capillary, an organic material used as the light reflective layer often has a thermal coefficient of expansion that is 100 times or more as large as that. For instance, silicon dioxide that is a typical material of the glass capillary has a thermal coefficient of expansion that is $5.6 \times 10^{-7}$/° C., whereas Teflon (registered trademark) AF as a typical example of the organic material used for the light reflective layer has a thermal coefficient of expansion that is $8.0 \times 10^{-5}$/° C. This means that the organic material used for the light reflective layer only repeats swelling and shrinking due to temperature change under the operation conditions and the environment where temperature changes severely. Since stress is locally concentrated a lot to the organic material in the long term, and so the organic material used for the light reflective layer falls off from the surface of the glass capillary and the amount of measurement light deteriorates. In this way, the conventional method including a light reflective layer made of air or an organic material at the outer wall of the channel fails to keep the conditions for total reflection in the vicinity of the joint part due to a reason resulting from the aforementioned physical properties of the materials and so has a problem of deterioration in sensitivity.

Due to such technical constraints, in order to meet the conditions for total light reflection of the measurement light 104, a conventionally configured flow cell of a type provided with a light reflective layer at the outer wall of the channel has to position the end face of the optical fiber 302 to the inside of the glass capillary from a part of the glass capillary 201 coming into contact with the joint part 306 as shown in FIG. 5. Such a configuration, however, has a small gap between the inner wall of the glass capillary 201 and the optical fiber 302 that is no larger than about a few tens microns, and so fine substances 507 such as fine filler particles, salt deposition or fine dust flowing into the flow cell are trapped at the gap. This phenomenon inhibits the flow of the solution 103 to cause a change in analysis value, and further leads to obstruction of the channel in the worst case and so leads to sudden elevation of the inner pressure of the flow cell and causes breakage of the flow cell.

Additionally, since a lower refractive index means higher propagation efficiency of measurement light, it is desirably to use air (refractive index 1) having the lowest refractive index from the viewpoint of sensitivity. On the other hand, since an organic material has a relatively high refractive index (refractive index 1.29 to 1.32), there is a problem of insufficient propagation efficiency of the measurement light.

In view of these problems, it is an object of the present invention to solve a problem of deterioration in sensitivity in the vicinity of a joint part of a type including a light reflective layer at the outer wall of the channel, and so provide a flow cell having high sensitivity.

Solution to Problem

A flow cell in a typical form of the present invention is disposed between a light source and a photodetector, and includes: a glass capillary having a sample channel through which measurement light propagated from the light source passes; an optical fiber, from which measurement light is incident on inside of the glass capillary; an optical element that receives measurement light passing through the inside of the glass capillary; a first pipe to introduce solution to the inside of the glass capillary; a second pipe to discharge solution passing through the glass capillary; a first joint part including a channel connecting the glass capillary, the optical fiber and the first pipe; and a second joint part including a channel connecting the glass capillary, the optical element and the second pipe. The glass capillary has an outer surface in contact with the first joint part or the second joint part, the outer surface being modified with an inorganic material layer to reflect the measurement light.

Preferably the inorganic material layer includes a layer containing inorganic substance particles and a binder as a main backbone and including voids filled with air. The inorganic substance particles desirably include inorganic oxide fine particles or inorganic fluorides fine particles, and the binder includes polymer having an alkoxysilane group or thermoplastic polymer.

Preferably the inorganic material layer has a surface modified with a reinforcement layer at a part in contact with the joint parts, and the reinforcement layer is made of a material that absorbs light at a wavelength band of ultraviolet, visible or infrared light.

Desirably the optical element is disposed coaxially with the central axis of the glass capillary, and the optical element includes an optical fiber, a window member or a lens. Desirably the optical element has a radius that is an outer radius of the glass capillary or more, and a distance from the optical element to an end face of the glass capillary is a value or less, the value being obtained by dividing a difference between the radius of the optical element and the outer radius of the glass capillary by tangent of an angle formed between a central axis of the glass capillary and measurement light emitted from the end face of the glass capillary.

Desirably the joint part is disposed so that the central axis of the channel and the central axis of the glass capillary are coaxial, the channel in the joint part has an inner radius that is a core radius of the optical fiber or more and an inner radius of the glass capillary or less, the core radius of the optical fiber is an outer radius of the glass capillary or less, and a distance from the optical fiber to the end face of the glass capillary is a value or less, the value being obtained by dividing a difference between the inner radius of the glass capillary and the core radius of the optical fiber by tangent of an angle formed between a central axis of the glass capillary and measurement light.

Advantageous Effects of Invention

The aforementioned problems can be solved by an inorganic material layer as a light reflective layer that reflects measurement light. That is, since the inorganic material layer has a melting point or a decomposition temperature that is sufficiently higher than the melting point of a thermal-dissolving resin that is used as a material of the joint parts, such a layer can maintain the function as the light reflective layer even when components are connected by thermal welding during the manufacturing of a flow cell. Since the glass capillary and the inorganic material have similar thermal coefficients of expansion, the inorganic material layer will not swell or shrink under operation conditions and environment where temperature changes severely, and so long-term stability of the performance can be achieved. These advantageous effects can be exerted the most when the inorganic material layer is made of silicon dioxide that is the same material as that of the glass capillary especially.

A layer containing inorganic substance particles and a binder as a main backbone and including voids filled with air may be used as the inorganic material layer. Thereby, air having the lowest refractive index can be captured in the light reflective layer, and so a low refractive index can be achieved as compared with a conventional organic material. This can increase the amount of measurement light that can propagate through the flow cell, and leads to improvement of sensitivity.

Additionally, a strength reinforcement layer absorbing light at a wavelength band of ultraviolet, visible or infrared light may be provided on the inorganic material layer. This can prevent external stray light while coping with fragility of the glass capillary. This also can lead to the advantageous effect of making the glass capillary thinner to increase the effective optical path length.

In the method of including a light reflective layer at the outer wall of the channel, an inorganic material layer is used as the light reflective layer, whereby total reflection light can be achieved at the joint part and optically optimized disposition of the components can improve propagation efficiency of the measurement light in the flow cell. That is, total reflection of light can be achieved at the contact face of the glass capillary outer face and the joint parts, which cannot be achieved at the conventional light reflective layer, and so components may be disposed on the joint part side where an optical element to receive the measurement light is disposed so as to receive the measurement light propagating through the glass capillary without loss, whereby sensitivity can be improved. On the joint part side where the optical fiber, from which measurement light is incident as well, components may be disposed to propagate the measurement light to the glass capillary without loss, whereby sensitivity can be improved. The thus optimized disposition of the optical elements leads to reduction of a narrowing part of the channel in the flow cell, and so can suppress clogging of the flow cell due to fine substances.

Problems, configurations, and advantageous effects other than those described above will be made clear by the following description of embodiments.

DESCRIPTION OF EMBODIMENTS

The following describes embodiments of the present invention, with reference to the drawings. The present invention can exert its advantageous effects from both of the methods to apply pressure to components during manufacturing of a flow cell for connection of the components without leakage and to include a joint part made of a thermal-dissolving resin for connection of components without leakage by thermal welding, and the advantageous effects can be exerted more from the latter method. Then the following description focuses on embodiments and drawings to manufacture a flow cell by thermal welding.

Figure 6:
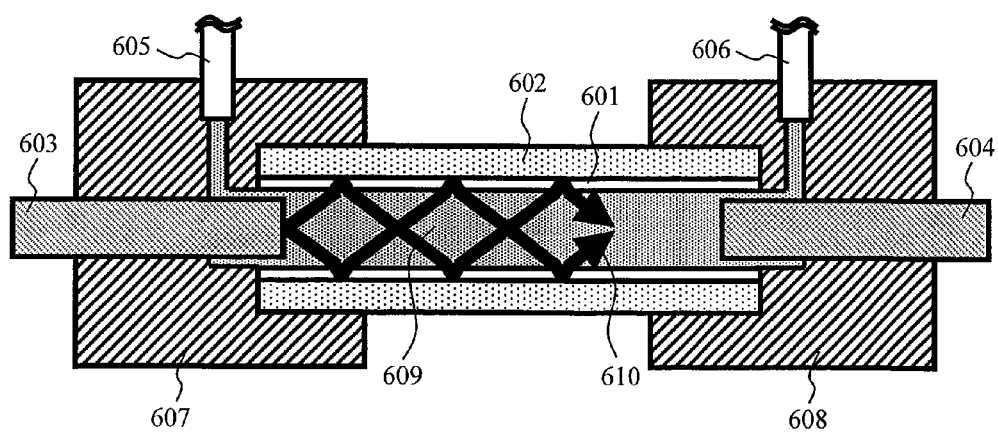
FIG. 6 is a cross sectional view showing an example of the flow cell according to the present invention.

FIG. 6 schematically shows one embodiment of a flow cell according to the present invention. This flow cell includes a glass capillary 601, an inorganic material layer 602 for surface modification of the glass capillary 601 to reflect measurement light, a first optical fiber 603 to introduce measurement light 610 into the glass capillary 601, a second optical fiber 604 to receive the measurement light 610 that travels through the glass capillary 601, a first pipe 605 to introduce solution 609 into the glass capillary 601, a second pipe 606 to discharge the solution 609 that travels through the glass capillary 601, and joint parts 607 and 608 having two channels connecting them. As described later, when the flow cell is assembled in a liquid analyzer, the measurement light 610 propagated from a light source is introduced into the glass capillary 601 through the optical fiber 603, propagates through the glass capillary due to the inorganic material layer 602, and is received by the optical fiber 604 for measurement by a detector. The solution 609 flowing through the pipe 605 is introduced into the glass capillary 601 via a sample channel in the joint part 607, and is discharged at the pipe 606 via a sample channel in the joint part 608.

The glass capillary 601 may be made of a material that does not absorb light at the wavelength band of ultraviolet, visible or infrared light, which includes quartz or molten silica that is a typical glass material, for example. The glass capillary has a cross-sectional shape that is a circular shape desirably to minimize the expanse of positional distribution of a sample by a rheological effect, which may be an elliptic shape or a polygonal shape. Specifically, the glass capillary preferably has an inner radius of 25 μm or more and 300 μm or less, and a thickness of 1 μm or more and 75 μm or less.

The inorganic material layer 602 may be made of a material having a refractive index lower than the refractive index of solution flowing through the glass capillary 601, a thermal coefficient of expansion that is similar to that of the glass capillary and a decomposition temperature sufficiently higher than the melting point of the thermal-dissolving resin. For instance, this may be desirably a layer made of an inorganic substance as a main backbone and having voids filled with air. Such a structure can achieve a value of the refractive index as the overall layer that is between the refractive index 1 of air and the refractive index of an inorganic material in accordance with the ratio of air in the layer, and that is lower than the refractive index 1.33 of water that is typically used for fluid analysis. Silica dioxide as a typical material that can implement such a structure has a melting point/decomposition temperature of 1,000° C. or higher, which is sufficiently higher than the melting point of polyether ether ketone resins that are often used as the thermal-welding resin, and has a similar thermal coefficient of expansion because it is the same material as that of the glass capillary. Such an inorganic material layer will not be decomposed even when high temperature that is higher than the melting point of the thermal-welding resin during manufacturing of the flow cell using thermal-welding is applied thereto, and so can keep the function as the light reflective layer. Such an inorganic material layer further will not swell or shrink under operation conditions and environment where temperature changes severely, and so the inorganic material layer will not fall off from the glass capillary after the long-term usage as well. This means that the amount of measurement light can be held at a constant value for a long term and the performance can be kept stably for a long term.

This layer is more desirable because the refractive index thereof can be freely changed by controlling the ratio of voids in the layer, and can achieve a refractive index that falls below the refractive index 1.29 of Teflon (registered trademark) AF that is generally used. This enables propagation of measurement light having a numerical aperture larger than that of conventional one and so can improve the sensitivity. An exemplary method to implement such a structure is to combine inorganic substance particles with a binder to fix them. For instance, desirable inorganic substance particles are silica dioxide (refractive index 1.46) particles and such a binder is polymer having an alkoxysilane group.

The following describes one example of the manufacturing process. N-butanol solution containing the mixture of silica dioxide particles with the average particle size of about 15 nm and silicon compound (silica sol) having hydrolysable residue (alkoxysilane group) is applied to the surface of a molten-silica capillary by dipping. After the application, condensation reaction is progressed for 30 minutes at 120° C., so as to form a polymer of the silica dioxide particles and the silicon compound and so form an inorganic material layer having a refractive index of 1.22.

In this way, the silica dioxide particles are disposed on the surface of the glass capillary at random and are allowed to bind, whereby a layer made of silica dioxide as a main backbone and having voids filled with air is formed. Other inorganic substance particles may include sodium hexafluoroalminate particles (refractive index 1.33) and inorganic fluorides such as calcium fluoride particles (refractive index 1.26), sodium fluoride particles or magnesium fluoride particles. Sodium hexafluoroalminate has a refractive index smaller than that of silica dioxide, and so a layer having a smaller refractive index can be formed by similar manufacturing process. These inorganic materials are appropriately selected depending on the prioritized performance while considering three factors of the melting point or the decomposition temperature, the thermal coefficient of expansion and the refractive index, and silica dioxide is particularly desirable.

Although inorganic oxide particles such as aluminum oxide, titanium oxide or cerium oxide may be used to achieve a low refractive index, silica dioxide having the same major component as that of the glass capillary can form a light reflective layer that bonds more firmly to the surface of the glass capillary, and so silica dioxide is desirably used as the main backbone. In order to prevent the mixture of a material of a reinforcement layer or other components into the voids of the layer having the voids and containing silica dioxide as a main backbone, the surface of the inorganic material layer is preferably coated with a layer of silica dioxide or a polymer layer. The inorganic material layer may be a metal deposited layer containing aluminum, rhodium, gold, or silver, although total reflection is not achieved in this case. The inorganic material layer desirably has a thickness of the wavelength of ultraviolet, visible or infrared light or more, i.e., 1 µm or more because it reflects light with the wavelength of ultraviolet, visible or infrared light.

A layer having a low refractive index similar to the above can be formed using hollow inorganic substance particles or aerosol. However, such hollow fine particles are fragile in mechanical strength, and so a layer including the combination of the aforementioned inorganic substance particles and a binder is preferable. Instead of particles as a main backbone, a homogeneous or equivalent periodic microstructure may be formed, from which similar advantageous effects can be obtained. This includes, for example, an inverted colloidal crystal structure, a gyroid structure, a nano-pillar structure or an inverted nano-pillar structure, which can be formed by phase separation using various polymer groups such as polystyrene and polymethyl methacrylate or lithography.

The optical fibers 603 and 604 may be fibers enabling propagation of measurement light at the wavelength band of ultraviolet, visible or infrared light without loss, and a quartz optical fiber is desirable, for example. Since the light amount has to be enough for improved sensitivity, they are preferably a multimode optical fiber to let as much light as possible propagate at a wide angle. For improved propagation efficiency of the light amount, the optical fibers preferably have a core radius that is an inner diameter of the glass capillary or less, which specifically may be 25 µm or more and 200 µm or less.

The pipes 605 and 606 desirably have as a small inner diameter as possible to suppress the expanse of positional distribution of a sample from a rheological viewpoint, which may be 25 µm or more and 300 µm or less in inner diameter, for example. They may be made of polyether ether ketone resin, a silica capillary surrounded with polyether ether ketone resin, Teflon resin or stainless-steel, for example. The pipes may have a shape in cross section that is desirably in a circular shape to minimize the expanse of positional distribution of a sample, which may be in an elliptic shape or a polygonal shape.

The joint parts 607 and 608 are provided with a sample channel therein, and have as a small inner diameter as possible to suppress the expanse of positional distribution of a sample, which may be specifically 25 µm or more and 300 µm or less in inner diameter. They may be made of a material absorbing light at the wavelength band of ultraviolet, visible or infrared light to avoid stray light from the outside, and desirably have chemical resistance. The sample channel may have a shape in cross section that is desirably in a circular shape to minimize the expanse of positional distribution of a sample by a rheological effect, which may be in an elliptic shape or a polygonal shape. Since minute sample channels have to be processed, they may be made of a hard material, which may be polyether ether ketone resin, Tefzel resin or stainless steel, for example. A material may be divided into two pieces and surfaces thereof may be ground, which are finally subjected to thermal welding, whereby a minute sample channel may be formed.

The joint parts 607 and 608 have a function to connect the glass capillary 601 provided with the inorganic material layer 602, the optical fibers 603, 604 and the pipes 605 and 606 without leakage. A method for the connection includes a mechanically crimping method and a thermally welding method as stated above. A typical method for mechanical crimping is to apply pressure using a ferrule and a nut so as to deform the ferrule elastically or plastically to seal a small gap. This method can use any material for the components, which may be polyether ether ketone resins or stainless steel, for example. A method for thermal welding includes irradiating contact parts of the joint parts, the glass capillary 601 provided with the inorganic material layer 602, the optical fibers 603, 604 and the pipes 605 and 606 with ultrasonic waves and laser or applying high-frequency magnetic field thereto so as to generate heat locally and to melt the joint parts 607 and 608 partially, thus sealing a small gap. This method requires a resin that can melt, e.g., polyether ether ketone resins to be used for the joint parts 607, 608. Additionally since there is a possibility that different types of materials fail to seal a small gap when they have a poor compatibility at their interface, the joint parts 607, 608 and the pipes 605, 606 are desirably made of the same material. For both of the connection methods, a larger bonding area of the joint parts 607, 608, the inorganic material layer 602, the optical fibers 603, 604 and the pipes 605 and 606 is preferable to seal a small gap sufficiently, and specifically a part bonded to the joint parts preferably has a length of 1 mm or longer.

The flow cell structure shown in FIG. 6 can maintain total reflection by the inorganic material layer even when dirt adheres externally to the outer face of the flow cell, and so the amount of measurement light does not decrease and the sensitivity will not be degraded.

The conventional flow cell structure including a light reflective layer at the outer wall of the channel has a plurality of problems resulting from its glass capillary. Since the glass capillary and the light reflective layer are made of a material that does not absorb light at the wavelength band of ultraviolet, visible or infrared light, a countermeasure against stray light is required, such as covering the surrounding of the flow cell with a material that absorbs light at the wavelength band of ultraviolet, visible or infrared light separately. Further, in the case of absorption spectroscopy that is widely used for spectroscopic analysis, sample solution does not absorb light when the measurement light passes through the glass capillary part, and so the effective optical path length will be lowered in accordance with the thickness of the glass capillary. Moreover, since the strength of the glass capillary is weak, the glass capillary may be broken under the condition as in a liquid chromatography analyzer having a flow cell receive a high internal pressure.

Figure 7:
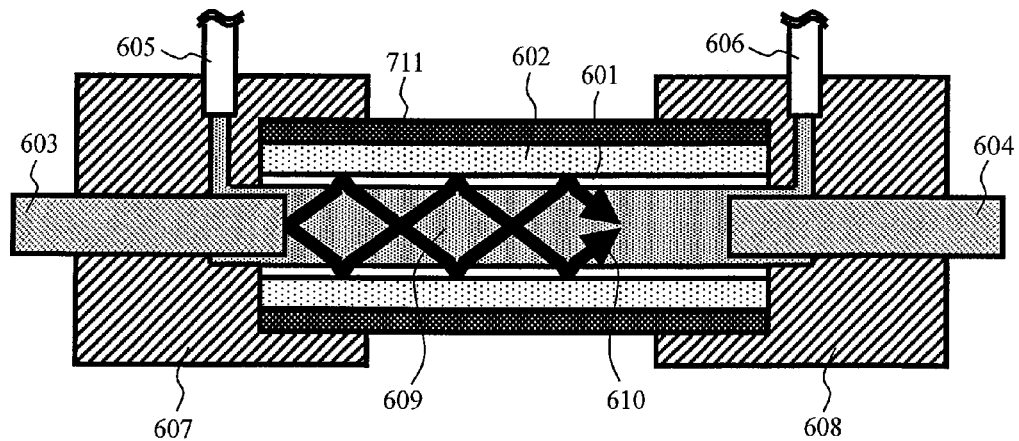
FIG. 7 is a cross sectional view showing another example of the flow cell according to the present invention.

These problems can be solved by modifying the surface of the inorganic material layer in the flow cell structure in FIG. 6 with a reinforcement layer. FIG. 7 is a schematic view thereof. A reinforcement layer 711 may be made of a material that absorbs light at the wavelength band of ultraviolet, visible or infrared light and can reinforce the strength of the glass capillary when it covers the outer face of the glass capillary, which is desirably a readily formable resin. For example, it includes polyimide resin, polyether ether ketone resin, Teflon resin, Tefzel resin, ABS resin and polyvinyl chloride resin, which are used alone, or resins including the mixture of the foregoing with carbon or glass fibers. When a higher internal pressure is applied as in a liquid chromatograph analyzer, polyether ether ketone resins are desirably used.

Such a reinforcement layer provided at the surface of the inorganic material can solve a plurality of problems resulting from the glass capillary. That is, this can prevent external stray light at the wavelength band of ultraviolet, visible or infrared light and can suppress the lowering of sensitivity. The reinforcement layer provided can improve the strength of the flow cell as a whole, and so the thickness of the glass capillary can be made thinner without breakage, and so the effective optical path length can be increased. Additionally, the reinforcement layer can prevent breakage of the glass capillary when external pressure is applied to the glass capillary at a part close to the joint parts. The inorganic material layer and the reinforcement layer modified at the outer wall face of the glass capillary facilitate the handling of the glass capillary, and eliminate the necessity to prepare for facilities such as a clean room to prevent contamination or to control the force applied minutely to prevent the breakage of the glass capillary, and so a flow cell can be manufactured at low cost and easily. When the glass capillary, the optical fibers, the pipes and the joint parts are connected by thermal welding, the reinforcement layer may be made of the same material as that of the joint parts, whereby a problem about compatibility at the interface can be avoided, and so the advantageous effect of connecting by thermal welding securely can be expected.

Figure 8:
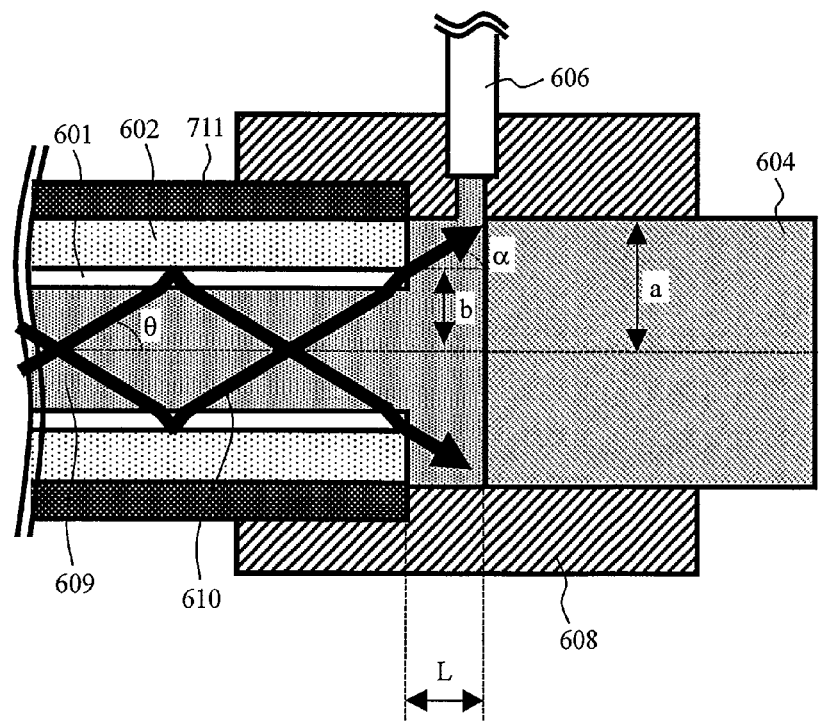
FIG. 8 is a cross sectional view showing the state of an exemplary joint part of the flow cell according to the present invention.

For more improved advantageous effects of the present invention, a positional relationship of the components in the joint parts has to be specified. Firstly, FIG. 8 shows the flow cell structure where the components are disposed for improved propagation efficiency of the measurement light, which focuses on the measurement light reception side.

For efficient capturing of the measurement light 610 that has propagated through the glass capillary 601, the optical fiber 604 on the reception side is preferably disposed coaxially with the glass capillary 601. In order to capture the measurement light 610 emitted from the end face of the glass capillary 601 efficiently, distance L from the end face of the optical fiber 604 to the end face of the glass capillary 601 is desirably optimized using the outer radius b of the glass capillary 601, the core radius a of the optical fiber 604 and the emission angle α of the measurement light 610 emitted from the end face of the glass capillary 601, thus defining a sample channel at the joint part 608. At this time, the core radius a of the optical fiber 604 on the reception side has to be the outer radius b of the glass capillary 601 or more.

In order to realize this, assuming that the emission angle α of the measurement light emitted from the end face of the glass capillary 601 is represented as in Expression 1 using the incident angle θ of the measurement light, the refractive index $n_1$ of the solution and the refractive index $n_2$ of the glass capillary 601, the distance L from the end face of the optical fiber to the end face of the glass capillary has to be optimized so as to meet Expression (2) using the core radius a of the optical fiber, the outer radius b of the glass capillary and the emission angle α of the measurement light 610 emitted from the end face of the glass capillary 601.

$$\alpha = \sin^{-1}\left(\frac{n_2}{n_1}\sin\left(\frac{\pi}{2} - \sin^{-1}\left(\frac{n_1}{n_2}\sin\left(\frac{\pi}{2} - \theta\right)\right)\right)\right) \quad (1)$$

$$L \le \frac{a-b}{\tan\alpha} \quad (2)$$

For instance, when a generally available quartz optical fiber of 500 μm in core radius having an allowable incident angle of about 12 and a glass capillary of 330 μm in outer radius are combined for use, the distance from the end face of the optical fiber to the end face of the glass capillary is desirably 0.3 mm or less. Such a structure enables capturing of the entire measurement light that has propagated through the glass capillary 601 and the amount of the light does not change even when the physical properties of internal solution 609 change.

When the optical fiber 604 is inserted into the glass capillary 601 as in FIG. 6, if physical properties of the internal solution 609 change, e.g., temperature changes and pressure changes or the composition of two types of solvent continuously changes as in a gradient method for a liquid chromatography analyzer, the amount of received light changes because optical intensity distribution changes at the end face of the optical fiber for reception or the position of the optical fiber end face changes due to pressure change, which may be often observed as noise or baseline wandering especially in absorption spectroscopy. The structure shown in FIG. 8 can keep the amount of reception light at the end face of the optical fiber constant even when physical properties of internal solution change, and so noise and baseline wandering can be reduced. As the pipe 606 on the solution discharge side connecting to the joint part 608 on the light reception side has a smaller diameter, a large internal pressure is applied to the main body of the flow cell and so pressure change inside the flow change increases and a change in the amount of received light at the optical fiber resulting from the change in physical properties of the internal solution as stated above increases. To avoid this, the pipe on the solution discharge side has a diameter that is larger than a diameter of the pipe on the solution introduction side, thus reducing internal pressure applied to the main body of the flow cell, whereby a change in the amount of received light at the optical fiber resulting from the change in physical properties of the internal solution can be suppressed. The thus movement of the position of the optical fiber from the inside of the glass capillary to the outside can reduce a narrowing part of the channel in the flow call, and so can prevent obstruction due to fine substances flowing through the flow cell.

Figure 9:
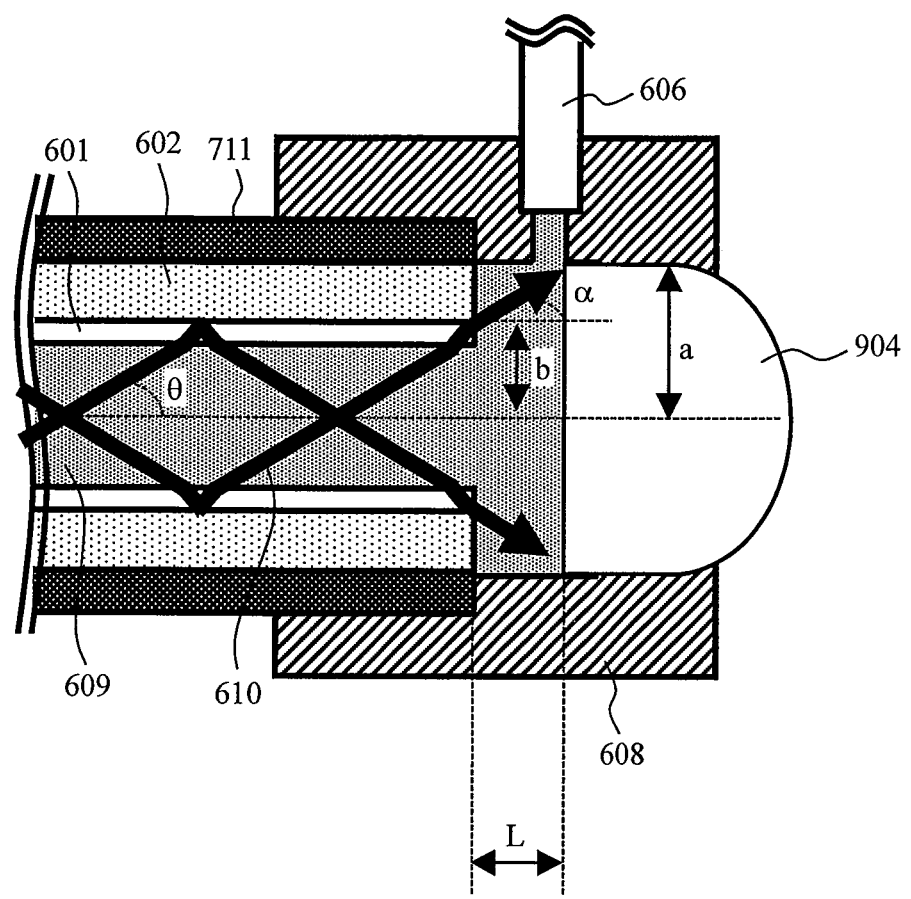
FIG. 9 is a cross sectional view showing the state of another exemplary joint part of the flow cell according to the present invention.

The aforementioned effects of improving propagation efficiency and reducing a change in the amount of received light can be exerted not only for an optical fiber as an optical element for light reception but also for optical elements 904 such as a simple window member, a flat convex lens, an aspherical lens, a ball lens, a rod lens or a cone lens as shown in FIG. 9. In this case, similarly to FIG. 8, the optical element 904 has to have a radius of the element a that is the outer radius b of the glass capillary 601 or larger, and the distance L from the end face of the optical element to the end face of the glass capillary has to be optimized so as to meet the same Expression (2) using the core radius a of the optical element 904, the outer radius b of the glass capillary and the emission angle α of the measurement light 610 emitted from the end face of the glass capillary 601. For instance, when a cylindrical window member of 3,000 μm in radius is used as an optical element having an incident angle of the measurement light of about 12 and a glass capillary of 330 μm in outer radius is used, the distance from the end face of the cylindrical window member to the end face of the glass capillary is desirably 4.6 mm or less. Such an optical element can increase the optimum distance from the end face of the optical element to the end face of the glass capillary based on Expression (2) because such an optical element typically has a larger radius than that of the core of an optical fiber.

Figure 10:
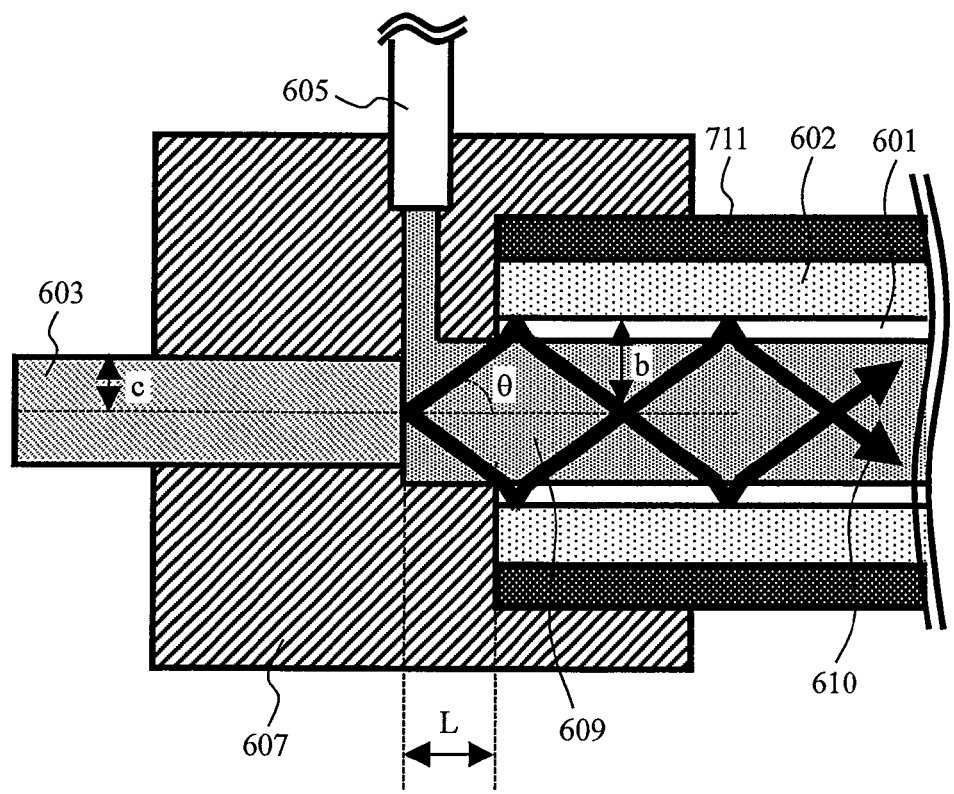
FIG. 10 is a cross sectional view showing the state of still another exemplary joint part of the flow cell according to the present invention.

Meanwhile, focusing on the incident side, in order to effectively capture the measurement light 610 emitted from the end face of the optical fiber 603, distance L from the end face of the optical fiber 603 to the end face of the glass capillary 601 is desirably optimized using the outer radius b of the glass capillary 601, the core radius c of the optical fiber 603, and the incident angle θ of the measurement light 610 as shown in FIG. 10, thus defining the sample channel at the joint part 607. That is, the distance L from the end face of the optical fiber 603 to the end face of the glass capillary 601 may meet Expression (3) using the core radius c of the optical fiber 603, the outer radius b of the glass capillary 601 and the incident angle θ of the measurement light.

$$L \le \frac{b-c}{\tan\theta} \quad (3)$$

For instance, when a generally available quartz optical fiber of 200 μm in core radius having an incident angle of about 12 and a glass capillary of 330 μm in outer radius are combined for use, the distance L from the end face of the optical fiber to the end face of the glass capillary is desirably 0.6 mm or less. Such a specified position of the optical fiber structure enables propagation of the measurement light without loss, and similarly to the reception side, moving of the position of the optical fiber from the inside of the glass capillary to the outside can reduce a narrowing part of the channel in the flow call, and so can prevent obstruction due to fine substances flowing through the flow cell.

Figure 11:
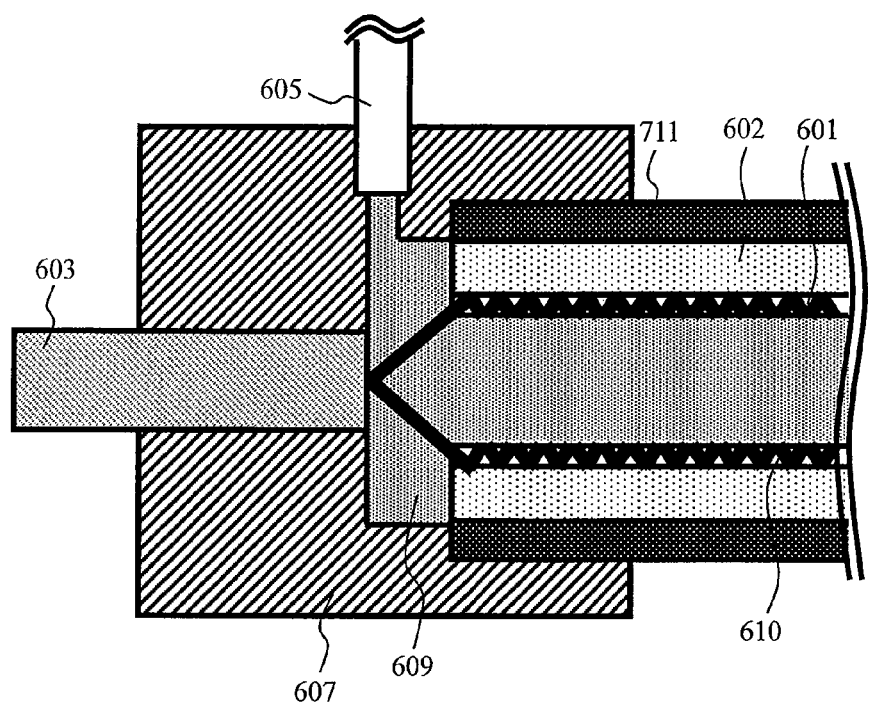
FIG. 11 is a cross sectional view to describe a problem of a joint part of the flow cell.

As shown in FIG. 11, when the end face of the glass capillary 601 is exposed to the sample channel in the joint part 607, the measurement light 610 is directly incident on the end face of the glass capillary, and so a component that does not pass through the sample channel in the glass capillary but propagates through a part of the glass capillary only increases, causing deterioration of sensitivity. To avoid this, as shown in FIG. 10, the end face of the glass capillary 601 is preferably sealed by providing, at the joint part, a sample channel with a step height having a diameter that is similar to the overall outer shape of the glass capillary 601 including the inorganic material layer 602 and the reinforcement layer 711 and with a diameter similar to the inner diameter of the glass capillary 601. That is, the end face of the glass capillary 601 is preferably configured to come into contact with the joint part 607 so as to prevent the measurement light from directly being incident from the end face on the inside of the glass wall making up the glass capillary.

The aforementioned advantageous effects from the components disposed in the joint parts are sufficient, whether either one of the structures or both of the structures may be used.

That is the description based on the assumption where the glass capillary 601 and the optical fiber 603 are disposed coaxially. The optical fiber 603 on the incident side may be disposed obliquely to the glass capillary 601. In this case, for efficient propagation of the measurement light, they are disposed preferably so that the total sum of the angle formed between the center axis of the glass capillary 601 and the center axis of the optical fiber 603 and the incident angle of the measurement light 610 becomes the critical angle of total reflection or less that is guaranteed by the inorganic material layer 602.

The aforementioned advantageous effects from the thus specified glass capillary and the optical fibers can be achieved by the modification of an inorganic material layer at the surface of the glass capillary that can totally reflects the measurement light. Considering the overall effect, the most desirable flow cell structure is such that the glass capillary is provided with the modification of the inorganic material layer and the reinforcement layer, the structure of FIG. 10 is used on the incident side of the measurement light and the structure of FIG. 8 or FIG. 9 is used on the reception side of the measurement light.

Figure 12:
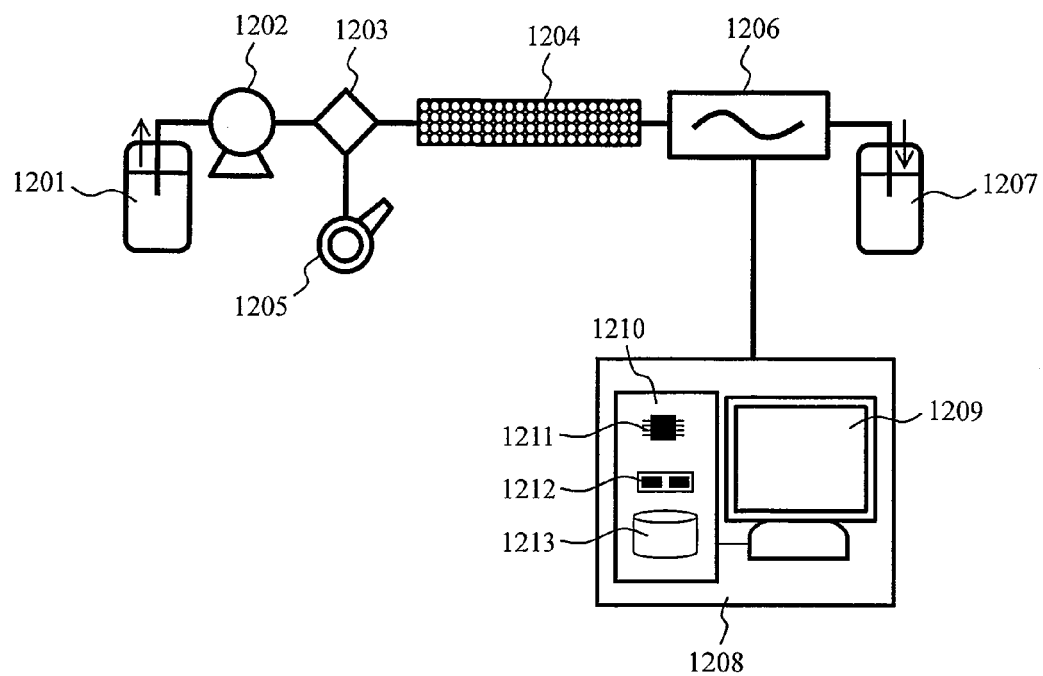
FIG. 12 shows the outline of a liquid analyzer including the flow cell of the present invention.
Figure 13:
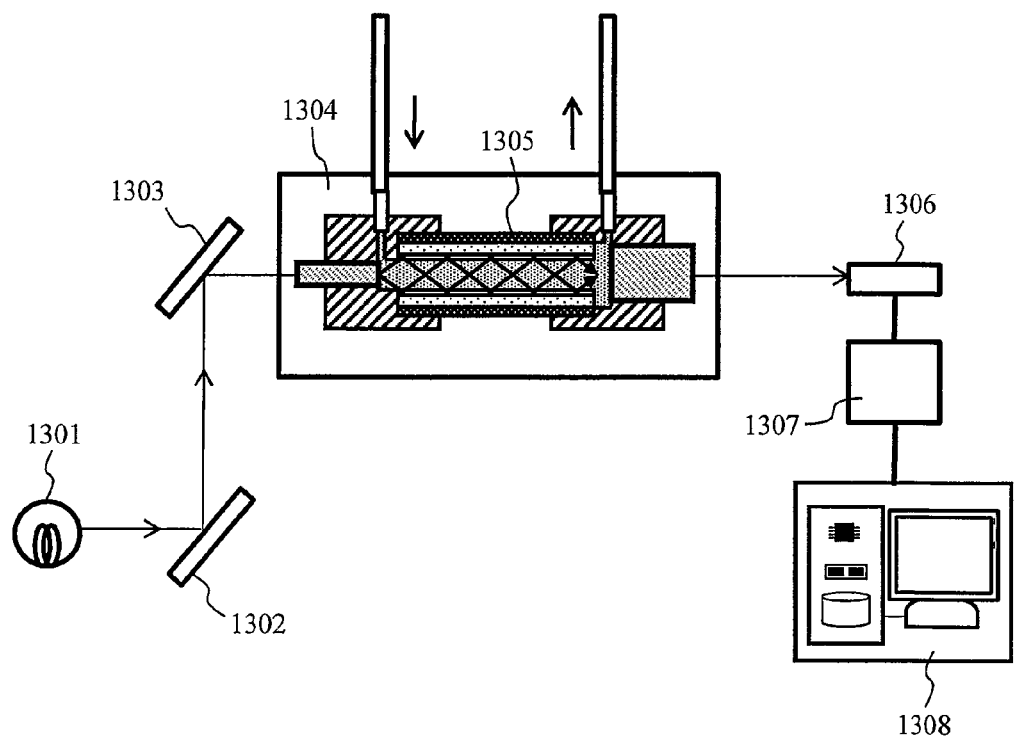
FIG. 13 shows the outline of a detector in a liquid analyzer including the flow cell of the present invention.
Figure 14:
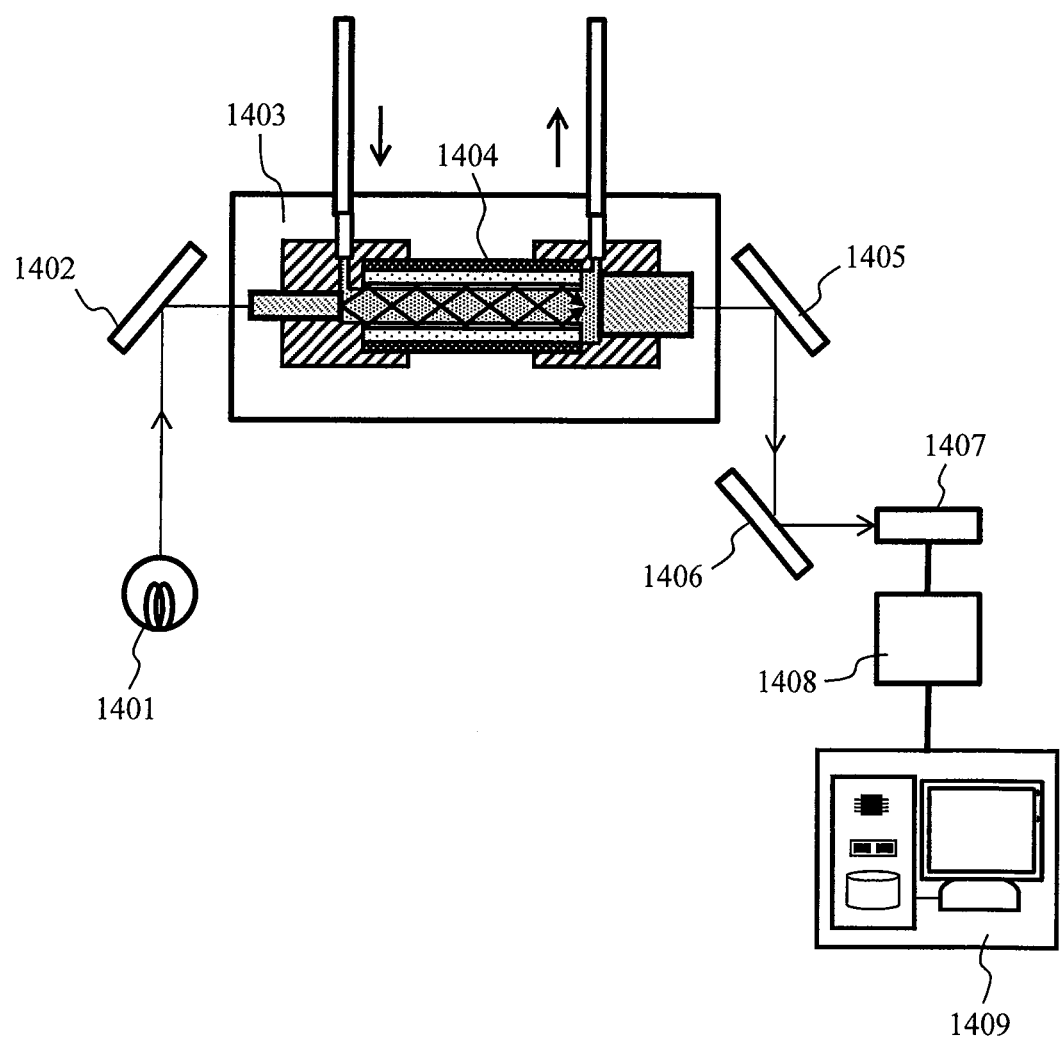
FIG. 14 shows the outline of another detector in a liquid analyzer including the flow cell of the present invention.

The flow cell according to the present invention may be assembled in a liquid analyzer such as for flow injection analysis or liquid chromatography to be used for spectroscopic analysis of a sample based on absorption or emission of light, for example. FIGS. 12 to 14 describe the case where a flow cell according to the present invention is assembled in a liquid analyzer.

FIG. 12 shows a channel system of a liquid chromatography analyzer. Eluant is sent from an eluant tank 1201 by a pump 1202, which is then supplied to a separation column 1204 via a sample introduction part 1203. A sample containing a test ingredient is introduced from an injector 1205, is subjected to component separation at the separation column 1204, and passes through a spectrophotometer 1206 to be discharged into a waste liquid tank 1207. The spectrophotometer 1206 is connected to a controller 1208. The controller 1208 may be a personal computer (PC) as shown in FIG. 12, for example. The PC includes a data display 1209 and a data processor 1210, where the data processor 1210 includes an arithmetic unit 1211, a temporary storage 1212 and a non-volatile memory 1213, for example.

FIG. 13 shows an optical system that can detect a specific wavelength in the spectrophotometer 1206 of FIG. 12. A flow cell 1305 has a structure including the combination of FIG. 8 and FIG. 10. Light from a light source 1301 passes through a condenser lens 1302 and is diffracted spectrally at a diffraction grating 1303. Then specific monochromatic light passes through an optical fiber in a flow cell 1305 fixed by a jig 1304 and then is applied into the glass capillary. Solution containing the sample liquated and separated from the separation column 1204 is supplied to the flow cell 1305 through a pipe, passes through the glass capillary, and is then discharged from the pipe. Measurement light passing through the glass capillary travels through the optical fiber and is received by a photodetector 1306, and the reception light signal is converted into absorbance at a detection circuit 1307 connected to a controller 1308. The light source 1301 used may be any light source that can emit light at an appropriate band, including a deuterium lamp or a halogen lamp. The photodetector 1306 used may be a photodetector that can detect light of a specific wavelength such as a silicon photodiode.

FIG. 14 is a schematic view of an optical system that can detect multi-wavelengths that is an exemplary liquid analyzer including a spectrophotometer in another form. A flow cell 1404 has a structure including the combination of FIG. 8 and FIG. 10. Light from a light source 1401 passes through a condenser lens 1402, then passes through an optical fiber in a flow cell 1404 fixed by a jig 1403 and is applied into the glass capillary. Solution containing the sample liquated and separated from a separation column 1204 is supplied to the flow cell 1404 through a pipe, passes through the glass capillary, and is then discharged from the pipe. Light passing through the glass capillary travels through the optical fiber and is received by a photodetector 1407 via a condenser lens 1405 and a diffraction grating 1406, and the reception light signal is converted into absorbance at a detection circuit 1408 connected to a controller 1409. The light source 1401 used may be any light source that can emit light at an appropriate band, including a deuterium lamp or a halogen lamp. The photodetector 1407 used may be a photodetector that can detect light of multi-wavelength such as a photodiode array.

Figure 1:
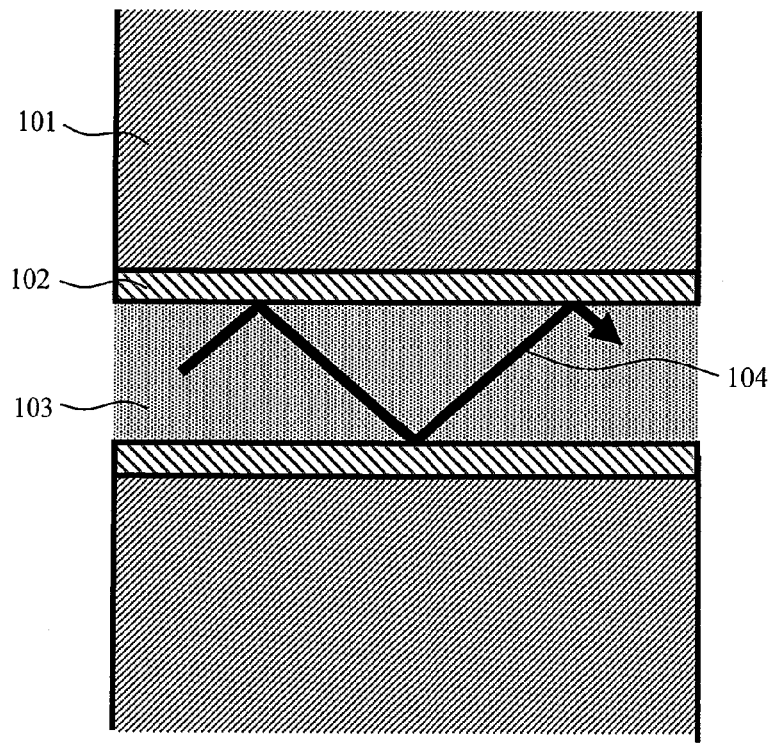
FIG. 1 schematically shows a conventional method for total reflection of light at an inner wall of a channel.
Figure 2:
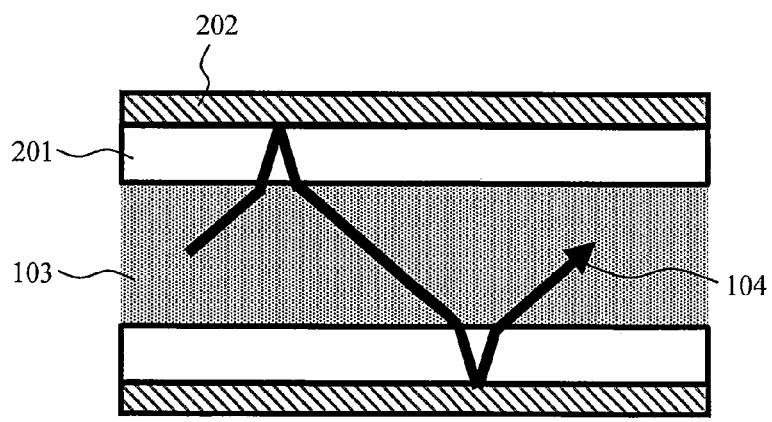
FIG. 2 schematically shows a conventional method for total reflection of light at an outer wall of a channel.
Figure 3:
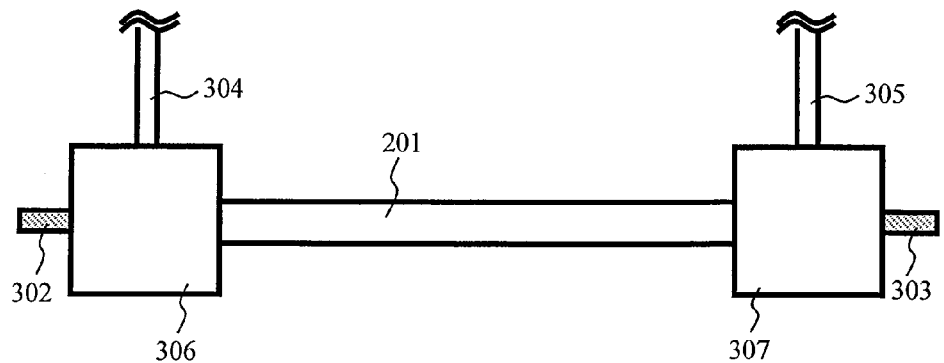
FIG. 3 shows the outline of a typical flow cell structure in a conventional method for total reflection of light at an outer wall of a channel.
Figure 4:
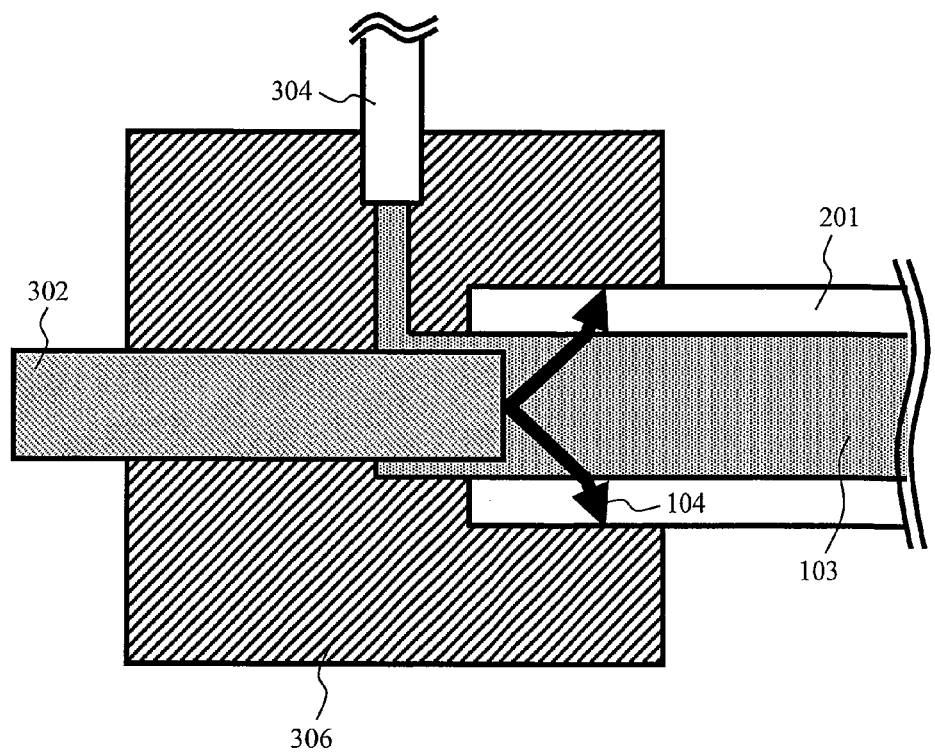
FIG. 4 is a cross sectional view showing the state of a joint part in a typical flow cell structure in a conventional method for total reflection of light at an outer wall of a channel.
Figure 5:
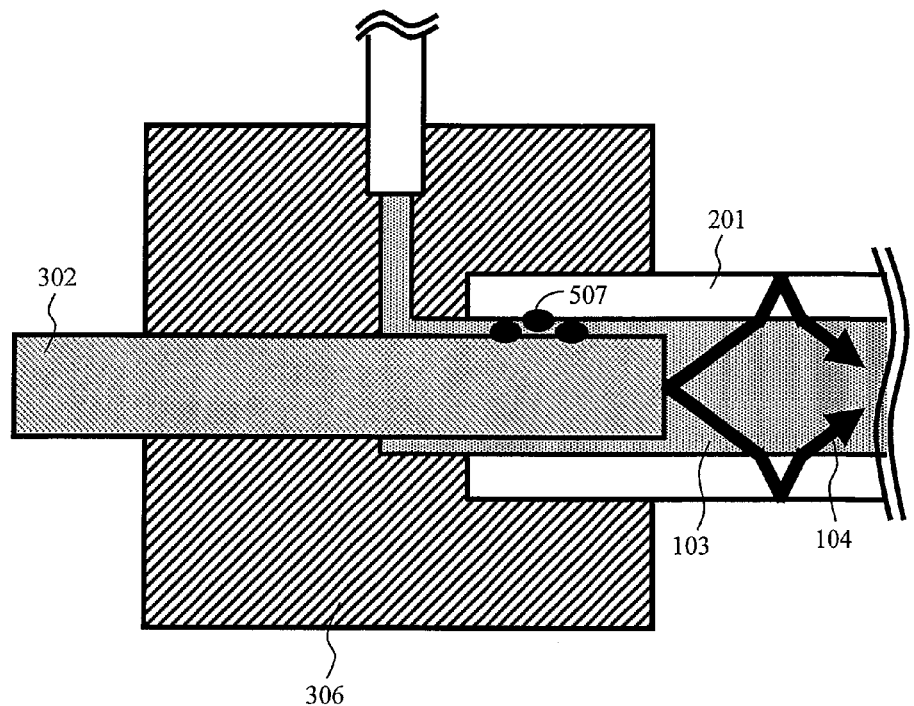
FIG. 5 is a cross sectional view showing the state of a joint part in a typical flow cell structure in a conventional method for total reflection of light at an outer wall of a channel.

The following describes an example of experiment to demonstrate the advantageous effects of the present invention. A flow cell (hereinafter called a flow cell 1 of the present invention) having the structure shown in FIG. 7 and a flow cell (hereinafter called a flow cell 2 of the present invention) having the structure including the combination of FIG. 8 and FIG. 10 were prepared using a molten silica capillary of 265 μm in inner radius and 65 μm in thickness as the glass capillary, a layer containing silica dioxide as a main backbone including the combination of silica dioxide nano-particles of about 15 nm and silica compound and voids filled with air as the inorganic material layer, a layer made of polyether ether ketone resin as the reinforcement layer, a multimode quartz optical fiber of a step-index type having a numerical aperture of 0.22 and core radius of 200 μm as the incident side optical fiber, a multimode quartz optical fiber of a step-index type having a numerical aperture of 0.22 and core radius of 500 μm as the light-reception side optical fiber, a pipe made of polyether ether resin of 0.1 mm in inner diameter as the pipe and a joint part made of polyether ether ketone resin having a sample channel of 0.5 mm in diameter as the joint part. The optical path length was specified as the distance between the end faces of the optical fibers, which was set at 50 mm. In order to connect the glass capillary, the optical fibers, the pipes and the joint parts without leakage, they were connected by thermal welding. Specifically the joint parts were heated at 370° C. or higher to melt the joint parts. For comparison, flow cells having the same structure that is the combination of FIG. 8 and FIG. 10 as that of the present invention were prepared using air and Teflon (registered trademark) AF as the light reflective layer at the surface of the glass capillary (hereinafter called comparative flow cell 1 and comparative flow cell 2, respectively). A conventional flow cell having the structure shown in FIG. 5 (hereinafter called a flow cell 3) also was prepared. Solvent that was charged in the flow cells was water for all of the flow cells.

The experiment was conducted using the liquid chromatography analyzer shown in FIG. 12 including the spectrophotometer shown in FIG. 13. The light source used was a halogen lamp. As stated above, a conventional method to implement total reflection of light at the outer wall of the channel has a problem that total reflection of light cannot be maintained at a part in the vicinity of the joint parts during manufacturing by thermal welding. Then, the amount of measurement light was compared among the flow cell 1 of the present invention, the conventional flow cell 1, the conventional flow cell 2 and the conventional flow cell 3. The result shows that, as compared with the amount of measurement light of the flow cell 1 of the present invention, the amount of measurement light was reduced to 32% for comparative flow cell 1 including the light reflective layer made of air and to 47% for comparative flow cell 2 including the light reflective layer made of Teflon (registered trademark). The amount of measurement light was similar between the flow cell 1 of the present invention and comparative flow cell 3. These results clearly show that the flow cell structure of the present invention can achieve total reflection of light in the vicinity of the joint parts.

Subsequently test for long-term stability of the performance of a flow cell structure of the present invention was performed under operation conditions and environment where temperature changes severely. Specifically cycle test was performed 300 times using flow cell 1 of the present invention and comparative flow cell 2, where temperature was rapidly changed between 0° C. and 100° C. The result shows that the amount of measurement light did not change for flow cell 1 of the present invention before and after the cycle test, and the amount of measurement light was reduced to 92% for comparative cell 2. This result means that the flow cell structure of the present invention can maintain the performance for a long term under operation conditions and environment where temperature changes severely.

Subsequently the following describes the advantageous effect of the flow cell structure of the present invention to optimize a positional relationship of the components. A comparison between flow cell 1 of the present invention and flow cell 2 of the present invention was made for the amount of measurement light, and the result shows that the amount of measurement light of flow cell 2 of the present invention was 178% of that of flow cell 1 of the present invention.

Subsequently the following describes a result of the experiment to demonstrate the advantageous effect of the present invention against external dirt. As a model for external dirt, a resin that absorbs light at the wavelength band of ultraviolet, visible or infrared light was used, and the amount of measurement light was compared between before and after dropping of the resin to the outer wall face of the glass capillary. The result shows that the amount of measurement light for comparative flow cell 1 was reduced to 13% after the dropping of dirt model, whereas the amount of measurement light for flow cell of the present invention did not change before and after the dropping of dirt model. Additionally the reinforcement layer used for this experiment was made of polyether ether ketone resin, and so stray light from the outside was not transmitted at all. Drop in pressure or leakage of liquid was not visually observed through the experiment, and so the glass capillary was not broken even when high internal pressure of about 10 MPa was applied thereto. Then, silica particles of 3 µm was allowed to flow through the flow cell as a model of clogging of fine substances, and there was no sign for clogging observed such as an abrupt increase in pressure.

The following describes the result of experiment about an increased effective optical path length because the glass capillary was made thinner. Experiment was conducted in the same configuration as that of the above experiment to measure effective optical path lengths using two types of glass capillaries having inner radius of 125 µm and thickness of 50 µm, and having inner radius of 90 µm and thickness of 85 µm, where the optical path length was set at 65 mm. The effective optical path length was compared using various densities of amide black ethanol solution, while comparing with an absorbance line for a 10 mm-cell in a typical absorptiometer. The result shows that the flow cell including the glass capillary having inner radius of 125 µm and thickness of 50 µm had the effective optical path length of 60.1 mm, and the glass capillary having inner radius of 90 µm and thickness of 85 µm had the effective optical path length of 52.4 mm. In this way, it was confirmed that a flow cell including a thinner glass capillary can increase the effective optical path length more. As stated above, the advantageous effects from the structure proposed by the present invention were confirmed from the experiments.

It was further confirmed that similar results can be obtained from flow cell structures shown in other drawings as well, instead of the flow cell structure including the combination of FIG. 8 and FIG. 10. Experiment under the same conditions was performed using a liquid chromatography analyzer shown in FIG. 12 including the spectrophotometer shown in FIG. 14, and it was confirmed that similar results can be obtained therefrom.

The present invention is not limited to the above-described embodiments, and may include various modification examples. For instance, the entire detailed configuration of the embodiments described above for explanatory convenience is not always necessary for the present invention. A part of one embodiment may be replaced with the configuration of another embodiment, or the configuration of one embodiment may be added to the configuration of another embodiment. The configuration of each embodiment may additionally include another configuration, or a part of the configuration may be deleted or replaced.

REFERENCE SIGNS LIST

101 Channel inner wall
102,202 Light reflective layer
103, 609 Solution
104, 610 Measurement light
201, 601 Glass capillary
602 Inorganic material layer
711 Reinforcement layer
302, 303, 603, 604 Optical fiber
304, 305, 605, 606 Pipe
306, 307, 607, 608 Joint part
507 Fine substance
904 Optical element
1201 Eluant tank
1202 Pump
1203 Sample introduction part
1204 Separation column
1205 Injector
1206 Spectrophotometer
1207 Waste liquid tank
1208, 1308, 1409 Controller
1209 Data display
1210 Data processor
1211 Arithmetic unit
1212 Temporary storage
1213 Non-volatile memory
1301, 1401 Light source
1302, 1402, 1405 Condenser lens
1303, 1406 Diffraction grating
1304, 1403 Jig
1305, 1404 Flow cell
1306, 1407 Photodetector
1307, 1408 Detection circuit

The invention claimed is:
1. A flow cell, comprising:
a glass capillary;
an optical fiber, from which measurement light is incident on inside of the glass capillary;
an optical element that receives measurement light passing through the inside of the glass capillary;
a first pipe to introduce solution to the inside of the glass capillary;

a second pipe to discharge solution passing through the glass capillary;

a first joint part including a channel connecting the glass capillary, the optical fiber and the first pipe; and a second joint part including a channel connecting the glass capillary, the optical element and the second pipe, wherein the glass capillary has an outer surface in contact with the first joint part or the second joint part, the outer surface being modified with an inorganic material layer to reflect the measurement light, and wherein the inorganic material layer includes inorganic particles and a binder as a main backbone and includes voids filled with air.

2. The flow cell according to claim 1, wherein the inorganic particles include inorganic oxide particles or inorganic fluoride particles, and wherein the binder includes a polymer having an alkoxysilane group or a thermoplastic polymer.

3. The flow cell according to claim 1, wherein the inorganic material layer further includes a reinforcement layer.

4. The flow cell according to claim 3, wherein the reinforcement layer includes polyether ether ketone resin, polyimide resin, Teflon resin, Tefzel resin, ABS resin or polyvinyl chloride resin.

5. The flow cell according to claim 3, wherein the reinforcement layer absorbs light at a wavelength band of ultraviolet, visible or infrared light.

6. The flow cell according to claim 1, wherein the optical element includes an optical fiber, a window member or a lens that is disposed coaxially with the glass capillary.

wherein the optical element has a radius that is equal to or greater than an outer radius of the glass capillary, and wherein a distance from the optical element to an end face of the glass capillary is less than or equal to a value obtained by dividing a difference between the radius of the optical element and the outer radius of the glass capillary by a tangent of an angle formed between a central axis of the glass capillary and measurement light emitted from the end face of the glass capillary.

7. The flow cell according to claim 1, wherein the optical fiber and the glass capillary are disposed coaxially, wherein the glass capillary has one end face that comes into contact with the first joint part, wherein channel in the first joint part that connects to the glass capillary has an inner radius that is greater than or equal to a core radius of the optical fiber and less than or equal to an inner radius of the glass capillary, wherein the core radius of the optical fiber is less than or equal to an outer radius of the glass capillary, and wherein a distance from the optical fiber to the end face of the glass capillary is less than or equal to a value obtained by dividing a difference between the inner radius of the glass capillary and the core radius of the optical fiber by a tangent of an angle formed between a central axis of the glass capillary and measurement light.

8. A liquid analyzer, comprising:
a light source;
a flow cell including:
a glass capillary,
an optical fiber, from which measurement light from the light source is incident on inside of the glass capillary, an optical element that receives measurement light passing through the inside of the glass capillary, a first pipe to introduce solution to the inside of the glass capillary, a second pipe to discharge solution passing through the glass capillary, a first joint part including a channel connecting the glass capillary, the optical fiber and the first pipe, and a second joint part including a channel connecting the glass capillary, the optical element and the second pipe; and a photodetector that receives measurement light from the optical element wherein the glass capillary has an outer surface in contact with the first joint part or the second joint part, the outer surface being modified with an inorganic material layer to reflect the measurement light, and wherein the inorganic material layer includes inorganic particles and a binder as a main backbone and includes voids filled with air.

9. The liquid analyzer according to claim 8, wherein the inorganic particles include inorganic oxide particles or inorganic fluoride particles, and wherein the binder includes a polymer having an alkoxysilane group or thermoplastic polymer.

10. The liquid analyzer according to claim 8, wherein the inorganic material layer further includes a reinforcement layer.

11. The liquid analyzer according to claim 10, wherein the reinforcement layer includes polyether ether ketone resin, polyimide resin, Teflon resin, Tefzel resin, ABS resin or polyvinyl chloride resin.

12. The liquid analyzer according to claim 8, wherein the optical element includes an optical fiber, a window member or a lens that is disposed coaxially with the glass capillary, wherein the optical element has a radius that is equal to or greater than an outer radius of the glass capillary, and wherein a distance from the optical element to an end face of the glass capillary is less than or equal to a value obtained by dividing a difference between the radius of the optical element and the outer radius of the glass capillary by a tangent of an angle formed between a central axis of the glass capillary and measurement light emitted from the end face of the glass capillary.

13. The liquid analyzer according to claim 8, wherein the optical fiber and the glass capillary are disposed coaxially, wherein the glass capillary has one end face that comes into contact with the first joint part, wherein the channel in the first joint part that connects to the glass capillary has an inner radius that is greater than or equal to a core radius of the optical fiber and less than or equal to an inner radius of the glass capillary, wherein the core radius of the optical fiber is less than or equal to an outer radius of the glass capillary, and wherein a distance from the optical fiber to the end face of the glass capillary is less than or equal to a value obtained by dividing a difference between the inner radius of the glass capillary and the core radius of the optical fiber by a tangent of an angle formed between a central axis of the glass capillary and measurement light.

* * * * *